(12) United States Patent
Narayanan et al.

(10) Patent No.: US 11,322,257 B2
(45) Date of Patent: May 3, 2022

(54) INTELLIGENT DIAGNOSIS SYSTEM AND METHOD

(71) Applicant: Novocura Tech Health Services Private Limited, Bangalore (IN)

(72) Inventors: Ajit Kumar Narayanan, Bangalore (IN); Monish Kaul, Bangalore (IN)

(73) Assignee: Novocura Tech Health Services Private Limited, Bangalore (IN)

( * ) Notice: Subject to any disclaimer, the term of this patent is extended or adjusted under 35 U.S.C. 154(b) by 416 days.

(21) Appl. No.: 16/264,723

(22) Filed: Feb. 1, 2019

(65) Prior Publication Data
US 2020/0020448 A1    Jan. 16, 2020

(30) Foreign Application Priority Data

Jul. 16, 2018 (IN) .............................. 201841026401

(51) Int. Cl.
*G16H 50/20* (2018.01)
*G16H 50/50* (2018.01)

(52) U.S. Cl.
CPC ............. *G16H 50/20* (2018.01); *G16H 50/50* (2018.01)

(58) Field of Classification Search
CPC ........ G16H 10/60; G16H 50/20; G16H 15/00; G16H 50/70; G16H 50/30; G16H 50/50; G16H 80/00; A61B 5/00
See application file for complete search history.

(56) References Cited

U.S. PATENT DOCUMENTS

| 2002/0002325 A1* | 1/2002 | Iliff | G16H 50/20 600/300 |
| 2002/0029157 A1* | 3/2002 | Marchosky | G16H 40/67 705/3 |

(Continued)

OTHER PUBLICATIONS

Halgren, S. L. (1993). In search of optimal human-expert system explanations: Empirical studies of human-human and human-expert system interactions (Order No. 9408625). Available from ProQuest Dissertations and Theses Professional. (304064589) (Year: 1993).*

*Primary Examiner* — Joseph D Burgess
(74) *Attorney, Agent, or Firm* — BakerHostetler

(57) ABSTRACT

An intelligent diagnosis system for diagnosing one or more health conditions is provided. The system comprises a plurality of preceptors configured to receive an initial set of parameters from a user, wherein the initial set of parameters represent at least one symptoms related to a health condition presented in a patient. The intelligent system further includes a cognition module coupled to the plurality of preceptors and configured to identify a first set of probable conditions based on the initial set of parameters and generate a set of reactions in response to the first set of probable conditions. The intelligent diagnosis system further includes a reaction module coupled to the cognition module and configured to select one or more reactions from the set of reactions and present the one or more reactions to the user. The cognition module is further configured to iteratively narrow down the initial set of probable conditions to a final set of probable conditions based on a final set of input parameters; wherein the final set of probable conditions is used to identify and diagnose the one or more health condition presented in the patient.

18 Claims, 5 Drawing Sheets

(56) References Cited

U.S. PATENT DOCUMENTS

| | | | |
|---|---|---|---|
| 2002/0040183 A1* | 4/2002 | Iliff | G16H 50/20 |
| | | | 600/300 |
| 2015/0272509 A1* | 10/2015 | Kwon | G06N 7/005 |
| | | | 600/518 |
| 2015/0310179 A1* | 10/2015 | Chengat | G16H 50/20 |
| | | | 705/3 |
| 2016/0180051 A1* | 6/2016 | Jellum | G06F 19/00 |
| | | | 703/2 |
| 2017/0124269 A1* | 5/2017 | McNair | G16H 10/60 |
| 2019/0108912 A1* | 4/2019 | Spurlock, III | G16B 40/20 |

* cited by examiner

INTELLIGENT DIAGNOSIS SYSTEM AND METHOD

PRIORITY STATEMENT

The present application claims priority under U.S.C. § 119 to Indian patent application number 201841026401 filed 16 Jul. 2018, the entire contents of which are hereby incorporated herein by reference.

BACKGROUND

The invention generally relates to healthcare systems and more particularly to a system and method for intelligent diagnosis of health conditions.

Medical diagnosis is a complex and challenging process as most symptoms and signs are non-specific. An error in diagnosis may result in the patient being denied timely and effective medical attention or being administered with incorrect medications and the consequences may be irreversible. The importance of reaching the correct diagnosis is key for fast and effective treatment.

Diagnostic opinion by medical practitioners and experts are often formed by patients' medical histories and symptoms. However, factors such as lack of understanding of the symptoms, poor communication, cognitive biases by medical experts, and other human errors often make it difficult for correct diagnosis. For example, physicians may give different credit and weightage to the specific symptoms and values. This not only leads to inaccurate diagnosis, but also such medical analyses are susceptible to differed interpretations among doctors. This imposes the need for an automated system that minimizes human bias and considers all relevant and irrelevant data objectively while in determining a diagnosis.

Recently, with the advancement in the computer technologies in the health system, various diagnostic systems have been developed to provide some aid to the medical experts in the diagnostic decision making process. However, advances in the learning sciences, such as clinical reasoning and processing, have not been utilized sufficiently and such systems focus on just one or few related diseases.

Moreover, existing diagnostic decision making systems are restricted to use of clinical rules and are not integrated into day to day operations and workflow of health organizations. In addition, existing systems lack interactive capability to develop a medical knowledge database.

Thus, there is a need of an interactive system that can automatically provide accurate and fast diagnosis using factual medical domain knowledge while minimizing human bias.

SUMMARY

The following summary is illustrative only and is not intended to be in any way limiting. In addition to the illustrative aspects, example embodiments, and features described, further aspects, example embodiments, and features will become apparent by reference to the drawings and the following detailed description. Example embodiments provide an automated medical diagnosis system and method.

Briefly, according to an example embodiment, an intelligent diagnosis system for diagnosing one or more health conditions is provided. The intelligent system comprises a plurality of preceptors configured to receive an initial set of parameters from a user, wherein the initial set of parameters represent at least one symptoms related to a health condition presented in a patient. The intelligent diagnosis system further includes a cognition module coupled to the plurality of preceptors and configured to identify a first set of probable conditions based on the initial set of parameters and generate a set of reactions in response to the first set of probable conditions. The intelligent diagnosis system further includes a reaction module coupled to the cognition module and configured to select one or more reactions from the set of reactions and present the one or more reactions to the user. The cognition module is further configured to iteratively narrow down the initial set of probable conditions to a final set of probable conditions based on a final set of input parameters; wherein the final set of probable conditions is used to identify and diagnose the one or more health condition presented in the patient.

In another embodiment, a method for diagnosing one or more health conditions is provided. The method comprises receiving an initial set of parameters from a user; wherein the initial set of parameters represent at least one symptoms related to a health condition presented in a patient. The method further includes identifying a first set of probable conditions based on the initial set of parameters, generating a set of reactions in response to the first set of probable conditions and selecting one or more reactions from the set of reactions and presenting the one or more reactions to the user. The method further includes iteratively narrowing down the initial set of probable conditions to a final set of probable conditions based on a final set of input parameters; wherein the final set of probable conditions is used to identify and diagnose the one or more health condition presented in the patient.

BRIEF DESCRIPTION OF THE FIGURES

These and other features, aspects, and advantages of the example embodiments will become better understood when the following detailed description is read with reference to the accompanying drawings in which like characters represent like parts throughout the drawings, wherein.

DETAILED DESCRIPTION OF EXAMPLE EMBODIMENTS

Figure 1:
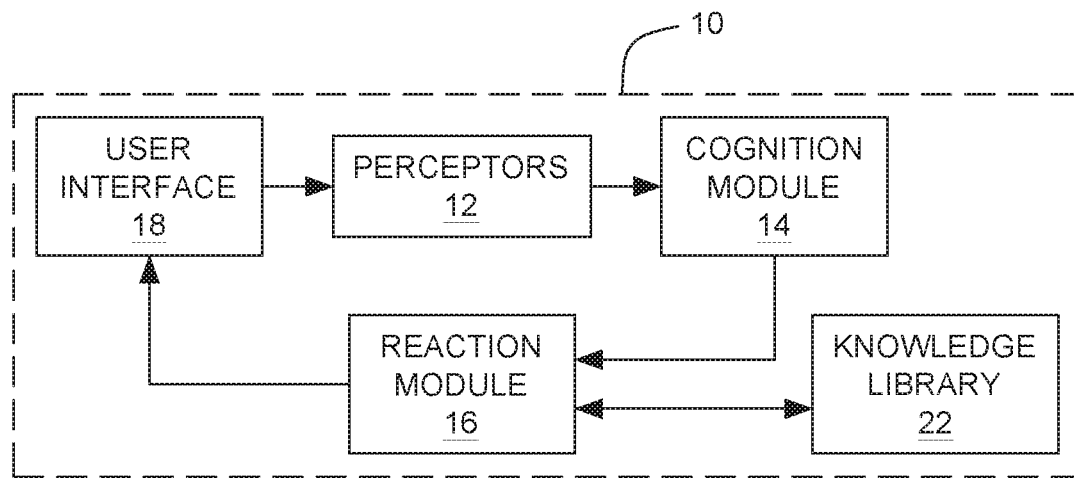
FIG. 1 is a block diagram of one embodiment of an automated intelligent diagnosis system, implemented according to the aspects of the present technique.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in many alternate forms and should not be construed as limited to only the example embodiments set forth herein.

Turning now to the drawings, FIG. 1 is a block diagram of one embodiment of an automated diagnosis system, implemented according to the aspects of the present technique. The system 10 includes preceptors 12, a cognition module 14 and a reaction module 16. Each block is described in further detail below.

In operation, a user is enabled to provide one or more symptoms related to a health conditions that is presented in a patient. In one embodiment, the one or more symptoms may be provided to via user interface 20. It may be noted that the user and the patient may or may not be the same entity. In some embodiments, the user is the patient. The user interface 20 may be voice based interface, text based interface, video based interface and/or combinations thereof. It may be further noted that the input parameters provided by the user may or may not be directly related to the health condition that the user is experiencing. Each component of the system 10 is described in further detail below.

Preceptors 12 is configured to receive an initial set of parameters from the user via a user interface 20. The initial set of parameters correspond to one or more symptoms that is experienced by the patient. In one embodiment, the initial set of parameters is extracted from free text chat stream, diagnostic data such as previous and current health reports, corresponding user health profile data, etc. provided by the user. In a further embodiment, the preceptors 12 includes a set of probes that receive input parameters and trigger a set of stimuli for the cognition module 14.

Cognition module 14 is coupled to preceptors 12 and is configured to identify a first set of probable conditions based on the initial set of parameters. The cognition module is further configured to generate a set of reactions in response to the first set of probable conditions identified from the initial set of parameters. Cognition module 14 is further configured to access medical data from various sources such as medical journals, databases, books, etc. In an embodiment, the medical data may include medical literature, case histories, diseases and related symptoms, related metadata information and the like.

Cognition module 14 is further configured to generate and store a master health list of all possible health conditions and a corresponding list of all possible symptoms. In one embodiment, the cognition module 14 is configured to identify the first set of probable conditions by mapping the initial set of parameters to the master list. It may be noted that master health list is continuously updated.

Reaction module 16 is communicatively coupled to the cognition module 14 and is configured to select one or more reactions from the set of reactions and present the one or more reactions to the user. In one embodiment, the reaction module selects the one or more reactions based on decision signals generated by knowledge library 22. The decision signals are generated based on prior knowledge of the probable set of health conditions associated with the provided symptoms.

The cognition module 14 along with the reaction module 16, is further configured to iteratively narrow down the initial set of probable conditions to a final set of probable conditions based on the inputs received in response to the one or more reactions presented to the users. The reaction module 16 is further configured to diagnose the one or more health condition presented in the patient from the final set of probable conditions. The manner in which the reaction module 16 determines the health conditions presented in the patient is described in further detail below.

Figure 2:
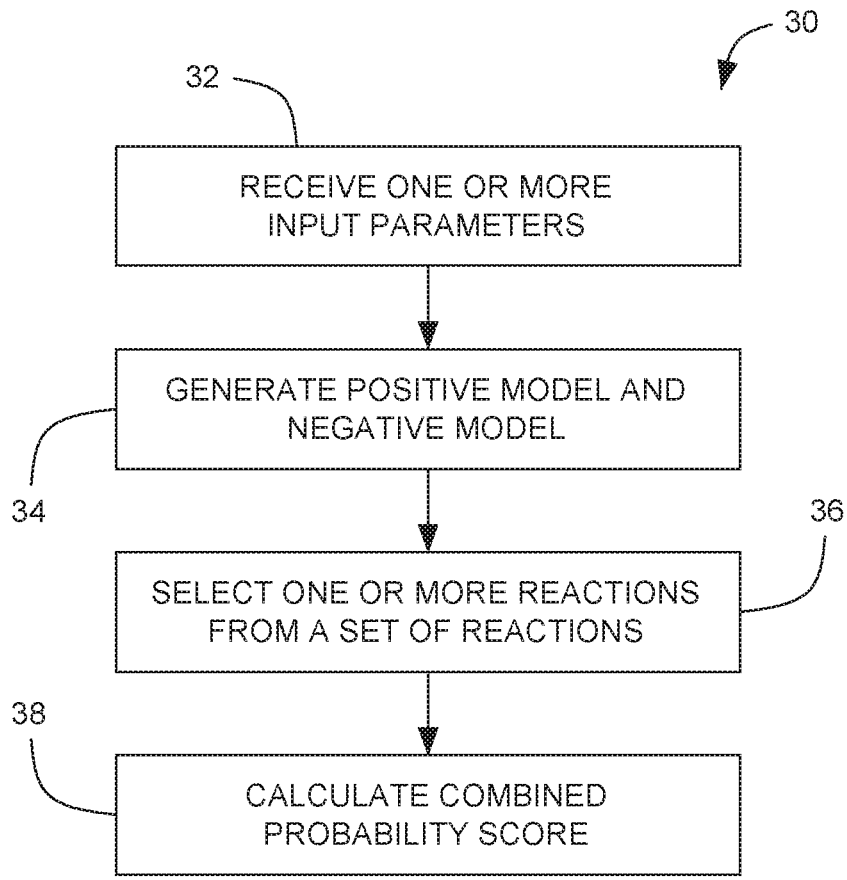
FIG. 2 is a flow diagram illustrating a process for diagnosing a health condition, implemented according to the aspects of the present technique.

FIG. 2 is a flow diagram illustrating a method to diagnose a health condition of a user, implemented according to the aspects of the present technique. The health condition is determined based on the symptom that may or may not be presented in the patient. The manner in which the health condition is diagnosed is described in further detail below.

At step 32, one or more input parameters is received. In one embodiment, the input parameters is an input query string received through a user interface. Further, a set of symptoms is extracted from the input parameters and an initial set of probable conditions is identified.

At step 34, a positive model and a negative model is generated for the set of symptoms identified in step 32. In one embodiment, the positive model and the negative model comprise a set of symptoms related to the initial set of probable conditions. It may be noted that, the positive model and the negative model may include overlapping symptoms and unique symptoms. Further, the negative model is built as an inverse of the positive model. In one embodiment, each symptom in the positive model is identified by a unique positive vector and each symptom in the negative model is identified by a unique negative vector. The positive model and the negative model are then used to generate a set of reactions for the initial set of parameters.

At step 36, one or more reactions are selected from the set of reactions and presented to the user. In one embodiment, the one or more reactions are selected based on decision signals. Further, the one or more reactions are represented in the form of one or more questions and presented to the user. In one embodiment, one or more positive vectors from the positive model are framed as questions related to the initial set of probable conditions identified in step 32. Similarly, the one or more negative vectors from the negative model are framed as questions that are unrelated to the initial set of probable conditions. The questions are provided to the user and steps 32 through 36 are repeated until a final set of probable conditions is identified.

At step 38, a combined probability score is calculated for the final set of probable conditions. In one embodiment, standard deviation is used to arrive upon the combined probability score. In a further embodiment, an aggression factor is applied to rank the final set of probable conditions. By applying the aggression factor, greater clarity is provided in identifying the health condition presented in the patient. The health condition is identified from the final set of probable conditions. Also, the aggression factor assists in arriving at the diagnosis faster. In a further embodiment, a convergence thresholding is performed. In one embodiment, most probable health conditions with a probability between a pre-defined top probability and a pre-defined top probability deviation may be used as threshold value. In one embodiment the threshold value is dynamic in nature.

As can be seen from the above description, the health condition of the patient is identified with help of constant interaction and using the information provided by the user at various stages. It may be noted that during the course of the interaction, the first set of probable conditions continuously changes until the final set of probable conditions is determined. The manner in which the intelligent diagnosis system interacts with a user is described in further detail below.

Figure 3:
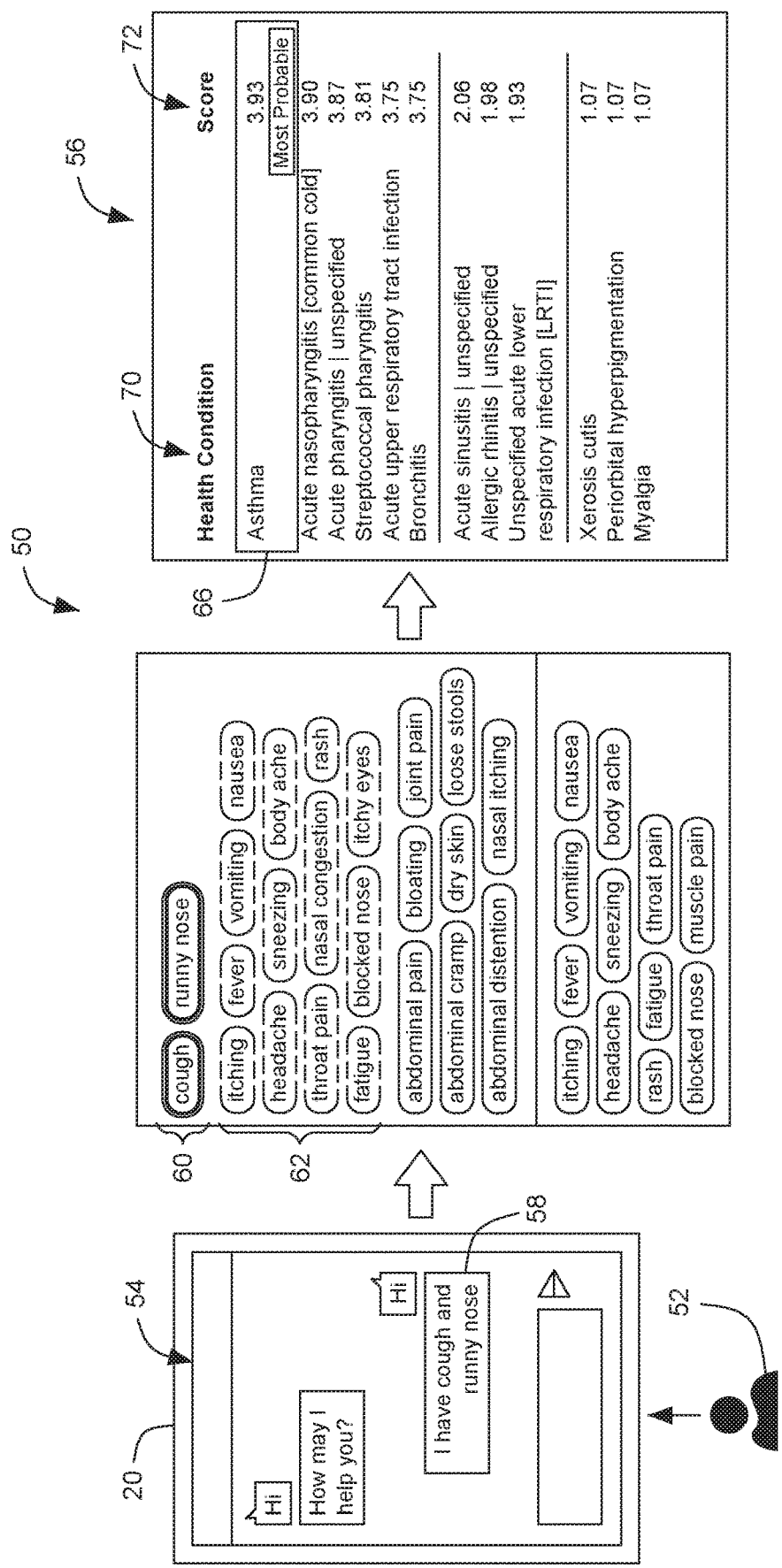
FIG. 3 through FIG. 5 illustrate example embodiments of a process for diagnosing a health condition, implemented according to the aspects of the present technique.
Figure 4:
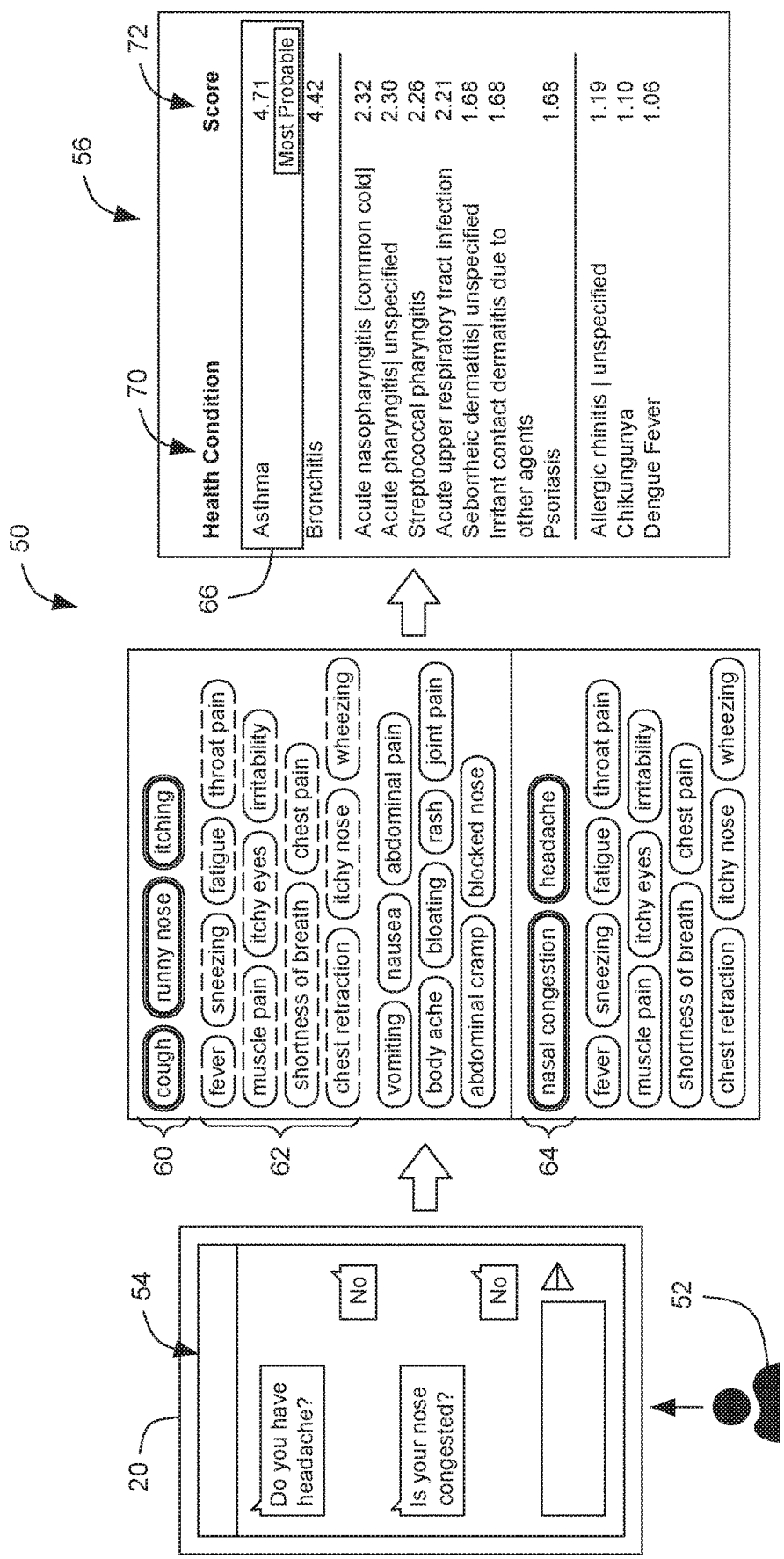
Figure 5:
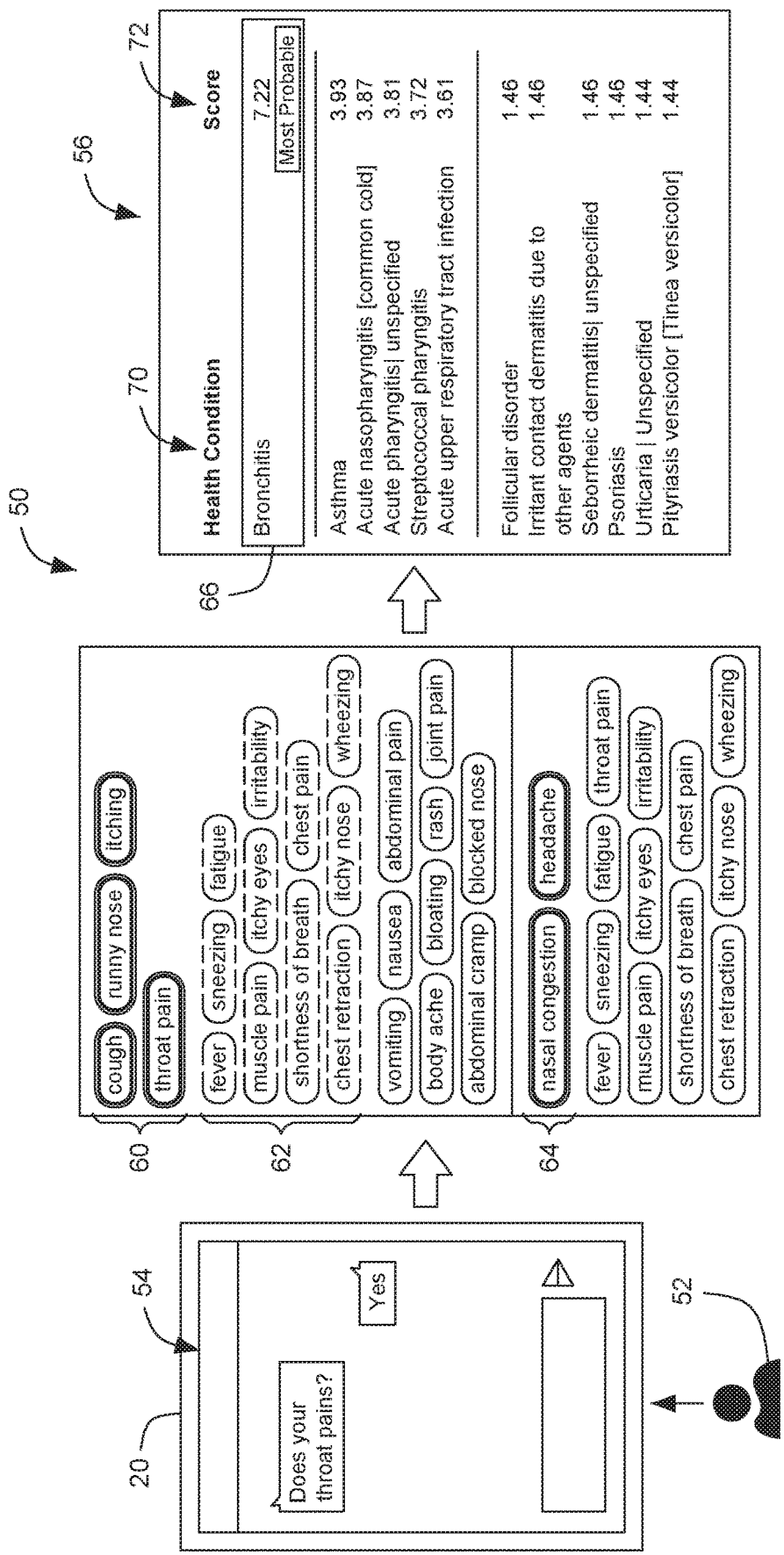

FIG. 3 through FIG. 5 illustrate example embodiments of a process for diagnosing a health condition, implemented according to the aspects of the present technique. In the illustrated embodiment, the input parameters provided by a user 52 are received through a user interface 20 such as a chat window 54. In the illustrated embodiment, the user 52 is enabled to provide input parameters 58 using free text chat streams. In the illustrated example, 'cough' and 'runny nose' are extracted as a set of symptoms 60. Further, a positive model 62 and a negative model 64 associated with the set of symptoms 60 is determined. In an embodiment, the positive model 62 and the negative model 64 includes overlapping symptoms such as fever and vomiting. The positive model 62 also have unique symptoms such as bloating and joint pain.

In one embodiment, a set of probable health conditions 70 are determined based on the initial set of symptoms. For example, the initial set of symptoms 60 ("cough" and "runny nose") leads to the set of probable health conditions such as "asthma", "common cold", "bronchitis". In this embodiment, the probable health conditions 70 are determined based on the combined probability score 72. The probable health condition with highest combined probability score is determined to be the most probable health condition 66 associated with the set of symptoms 60. In this example "asthma" is determined to be the most probable health condition with the combined probability score of about '3.93' followed by "acute nasopharyngitis" with probability score of about '3.90'.

Further, the system 50 iteratively communicates with the user 52 based on a set of reactions related to the positive model and negative model. In this example, the user provides further inputs based on the set of reactions that appear as questions such as "do you have a headache". The answers provided by the user is used to correlate the symptoms and move closer to the most probable health condition 6. The answers provided by the users also assists in moving away from the conditions which are not related to set of symptoms. The value of the combined probability score is updated with each iterative set of reactions. In addition, the positive model 62 and negative model 64 are updated with each iteration. As shown in the example, the value of the combined probability score for most probable health condition has increased from '3.93' to '4.71'. It may be noted that the second most probable health condition has changed from "acute nasopharyngitis" to "bronchitis" with combined probability score of about '4.42'.

With further real-time communication with the user 52, the final set of probable conditions are calculated. In this example, the set of symptoms 60 are now determined to be "cough", "runny nose", "itching" and "throat pain". Based upon the set of symptoms 60, the value of the combined probability score is updated. In addition, the positive model 62 and negative model 64 are updated. As shown in the example, the most probable health condition is determined to be "bronchitis" with the highest combined probability score of about 7.72 followed by "asthma" with the combined probability score of about '3.93' and so forth. It may be noted that at the end of the process, a diagnosis of the health condition with a highest probability of occurrence is provided to the user 52.

Figure 6:
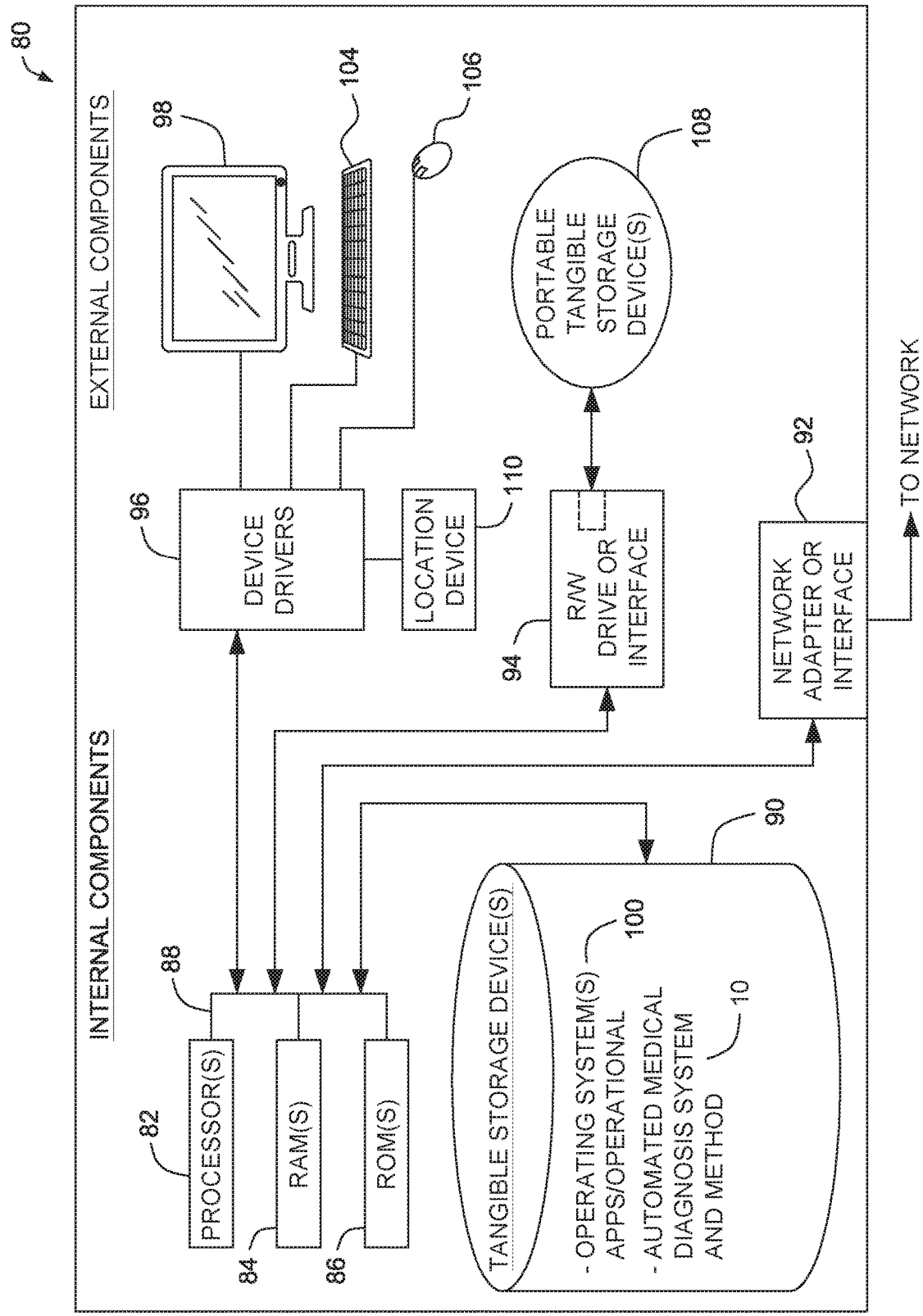
FIG. 6 is a block diagram of an embodiment of a computing device in which the modules of the automated diagnosis system, described herein, are implemented.

The modules of the intelligent diagnosis system 10 described herein are implemented in computing devices. One example of a computing device 80 is described below in FIG. 6. The computing device includes one or more processor 82, one or more computer-readable RAMs 84 and one or more computer-readable ROMs 86 on one or more buses 88. Further, computing device 80 includes a tangible storage device 90 that may be used to execute operating systems 100 and the automated diagnosis system 10. The various modules of the system 10 includes preceptors 12, a cognition module 14 and a reaction module 16.

The modules may be stored in tangible storage device 90. Both, the operating system 100 and the system 10 are executed by processor 82 via one or more respective RAMs 84 (which typically include cache memory). The execution of the operating system 100 and/or the system 10 by the processor 82, configures the processor 82 as a special purpose processor configured to carry out the functionalities of the operation system 100 and/or the automated diagnosis system 10, as described above.

Examples of storage devices 90 include semiconductor storage devices such as ROM 86, EPROM, flash memory or any other computer-readable tangible storage device that may store a computer program and digital information.

Computing device also includes a R/W drive or interface 94 to read from and write to one or more portable computer-readable tangible storage devices 108 such as a CD-ROM, DVD, memory stick or semiconductor storage device. Further, network adapters or interfaces 92 such as a TCP/IP adapter cards, wireless Wi-Fi interface cards, or 3G or 4G wireless interface cards or other wired or wireless communication links are also included in computing device.

In one example embodiment, the intelligent diagnosis system 10 includes preceptors 12, a cognition module 14 and a reaction module 16, and may be stored in tangible storage device 108 and/or may be downloaded from an external computer via a network (for example, the Internet, a local area network or other, wide area network) and network adapter or interface 92.

Computing device further includes device drivers 96 to interface with input and output devices. The input and output devices may include a computer display monitor 98, a keyboard 104, a keypad, a touch screen, a computer mouse 106, and/or some other suitable input device. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present.

The afore mentioned description is merely illustrative in nature and is in no way intended to limit the disclosure, its application, or uses. The broad teachings of the disclosure may be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the example embodiments is described above as having certain features, any one or more of those features described with respect to any example embodiment of the disclosure may be implemented in and/or combined with features of any of the other embodiments, even if that combination is not explicitly described. In other words, the described example embodiments are not mutually exclusive, and permutations of one or more example embodiments with one another remain within the scope of this disclosure.

While only certain features of several embodiments have been illustrated, and described herein, many modifications and changes will occur to those skilled in the art. It is, therefore, to be understood that the appended claims are intended to cover all such modifications and changes as fall within the true spirit of inventive concepts.

The invention claimed is:

1. A system for diagnosing one or more health conditions, the system comprising:
 a user interface configured to receive an initial set of parameters from a user, wherein the initial set of parameters represent at least one symptom related to one or more health conditions of a patient;
 a plurality of preceptors configured to receive the initial set of parameters from the user interface;
 a cognition unit configured to receive the initial set of parameters from the plurality of preceptors and configured to identify a first set of probable conditions based on the initial set of parameters and to generate a set of reactions based on the first set of probable conditions, wherein the cognition unit is configured to generate a positive model and a negative model, wherein the positive model and the negative model comprise a first set of symptoms related to the first set of probable conditions, and wherein each of the positive and negative models comprises a second set of symptoms different from the first set of symptoms and the second set of symptoms of the other model; and
 a reaction unit configured to receive the set of reactions from the cognition unit and configured to select one or more reactions from the set of reactions and present the one or more reactions to the user,
 wherein the cognition unit is further configured to iteratively narrow down the first set of probable conditions to a final set of probable conditions based on a final set of input parameters, the final set of input parameters being different from the initial set of parameters,
 wherein the positive model and the negative model are updated after each of the iterations,
 wherein a plurality of positive vectors from the positive model is framed as questions related to the first set of probable conditions,
 wherein a plurality of negative vectors from the negative model is framed as questions unrelated to the first set of probable conditions, and
 wherein the final set of probable conditions is used to identify and diagnose the one or more health conditions presented in the patient.

2. The system of claim 1, wherein the plurality of preceptors are configured to receive continuously a set of answers in response to the one or more reactions continuously presented to the user, and wherein the final set of input parameters are derived from the set of answers provided by the user.

3. The system of claim 1, wherein each symptom in the positive model is identified by one of the unique positive vectors and each symptom in the negative model is identified by one of the unique negative vectors.

4. The system of claim 1, wherein the final set of probable conditions is based on a combined probability score derived from the first set of probable conditions.

5. The system of claim 4, wherein the cognition unit is configured to calculate an aggression factor to determine the final set of probable conditions.

6. The system of claim 5, further comprising a knowledge library configured to receive the set of reactions from the reaction unit and configured to generate a plurality of decision signals from the set of reactions generated by the cognition unit.

7. The system of claim 6, wherein the knowledge library is configured to continuously learn, map and store a reaction map, wherein the reaction map comprises a set of possible health conditions mapped to a set of possible reactions.

8. The system of claim 6, wherein the reaction unit is further configured to select one or more reactions from the set of reactions generated by the cognition unit based on the plurality of decision signals.

9. The system of claim 1, wherein the set of reactions presented to the user are represented in the form of one or more questions.

10. A method for diagnosing one or more health conditions, the method comprising:
 receiving, from a user interface, an initial set of parameters from a user, wherein the initial set of parameters represent at least one symptom related to a health condition presented in a patient;
 identifying a first set of probable conditions based on the initial set of parameters;
 generating a positive model and a negative model, wherein the positive model and the negative model comprise a first set of symptoms related to the first set of probable conditions, wherein each of the positive and negative models comprises a second set of symptoms different from the first set of symptoms and the second set of symptoms of the other model;
 generating a set of reactions to based on the first set of probable conditions;
 selecting one or more reactions from the set of reactions and presenting the one or more reactions to the user; and
 iteratively narrowing down the first set of probable conditions to a final set of probable conditions based on a final set of input parameters, the final set of input parameters being different from the initial set of parameters,
 wherein the positive model and the negative model are updated after each of the iterations,
 wherein a plurality of positive vectors from the positive model is framed as questions related to the first set of probable conditions,
 wherein a plurality of negative vectors from the negative model is framed as questions unrelated to the first set of probable conditions, and
 wherein the final set of probable conditions is used to identify and diagnose the one or more health conditions presented in the patient.

11. The method of claim 10, further comprising continuously receiving a set of answers in response to the one or more reactions presented to the user, wherein the final set of input parameters are derived from the set of answers provided by the user.

12. The method of claim 10, wherein each symptom in the positive model is identified by one of the unique positive vectors and each symptom in the negative model is identified by one of the unique negative vectors.

13. The method of claim 12, wherein the final set of probable conditions is based on a combined probability score.

14. The method of claim 13, further comprising calculating an aggression factor to determine the final set of probable conditions.

15. The method of claim 14, further comprising generating a plurality of decision signals for the set of reactions, wherein the plurality of decision signals are generated based on historical data.

16. The method of claim 15, further comprising continuously learning, mapping, updating and storing a reaction map, wherein the reaction map comprises a set of possible health conditions mapped to a set of possible reactions.

17. The method of claim 15, further comprising selecting one or more reactions from the set of reactions generated based on the plurality of decision signals.

18. The method of claim 10, wherein the set of reactions presented to the user are represented in the form of one or more questions.

* * * * *